US012766289B2

(12) United States Patent
Matsuda et al.

(10) Patent No.: US 12,766,289 B2
(45) Date of Patent: Oct. 20, 2026

(54) DOUBLE-LUMEN CATHETER

(71) Applicant: NIPRO CORPORATION, Osaka (JP)

(72) Inventors: Yusuke Matsuda, Osaka (JP); Takuma Nakamura, Osaka (JP); Yuya Fujiki, Osaka (JP); Shota Nakai, Osaka (JP)

(73) Assignee: NIPRO CORPORATION, Osaka (JP)

( * ) Notice: Subject to any disclaimer, the term of this patent is extended or adjusted under 35 U.S.C. 154(b) by 1176 days.

(21) Appl. No.: 17/615,478

(22) PCT Filed: May 29, 2020

(86) PCT No.: PCT/JP2020/021372
§ 371 (c)(1),
(2) Date: Nov. 30, 2021

(87) PCT Pub. No.: WO2020/250717
PCT Pub. Date: Dec. 17, 2020

(65) Prior Publication Data

US 2022/0233809 A1 Jul. 28, 2022

(30) Foreign Application Priority Data

Jun. 11, 2019 (JP) ................................ 2019-108759

(51) Int. Cl.
*A61M 25/00* (2006.01)
*A61M 25/01* (2006.01)

(52) U.S. Cl.
CPC ...... *A61M 25/003* (2013.01); *A61M 25/0194* (2013.01); *A61M 2025/0031* (2013.01)

(58) Field of Classification Search
CPC ............ A61M 25/003; A61M 25/0194; A61M 2025/0031; A61M 25/007; A61M 2025/0037; A61M 1/3659; A61M 1/3661
See application file for complete search history.

(56) References Cited

U.S. PATENT DOCUMENTS 5,569,182 A * 10/1996 Twardowski ....... A61M 1/3658 604/523
7,128,734 B1 * 10/2006 Wilson ............... A61B 17/3415 604/93.01

(Continued)

FOREIGN PATENT DOCUMENTS

EP 3071284 9/2016
JP H11-503336 A 3/1999

(Continued)

OTHER PUBLICATIONS

English Translation of Matsuda (JP 2018198930) (Year: 2018).*

(Continued)

*Primary Examiner* — Courtney Fredrickson
(74) *Attorney, Agent, or Firm* — Renner, Otto, Boisselle & Sklar LLP

(57) ABSTRACT

A double lumen catheter includes: a circumferential wall 101 forming a lumen extending from a proximal end to a distal end; and a partition 102 dividing the lumen into a first passage 110 and a second passage 120 extending in a longitudinal direction. Distal ends of the first passage 110 and the second passage 120 of the circumferential wall 101 are aligned with each other. The partition 102 includes a projection 103 projecting beyond the distal end of the circumferential wall 101, and having a U-shaped plane. The first passage 110 has, at the distal end, a first passage slit 111 formed by cutting out a part of the circumferential wall 101 around a circumferential center of the circumferential wall 101.

8 Claims, 8 Drawing Sheets

(56) References Cited

U.S. PATENT DOCUMENTS

| | | | | |
|---|---|---|---|---|
| 10,143,822 | B2 * | 12/2018 | Sansoucy | A61M 1/3661 |
| 2005/0070842 | A1 | 3/2005 | Lotito | |
| 2008/0097409 | A1 | 4/2008 | Stephens | |
| 2009/0112153 | A1 | 4/2009 | Gregersen | |
| 2009/0118661 | A1 * | 5/2009 | Moehle | A61M 25/0032 604/6.16 |
| 2010/0081986 | A1 * | 4/2010 | Matson | A61M 25/0075 604/247 |
| 2011/0172642 | A1 * | 7/2011 | Lareau | A61M 25/0017 604/523 |
| 2013/0046224 | A1 * | 2/2013 | Ravenscroft | A61M 25/0026 604/28 |
| 2013/0085477 | A1 * | 4/2013 | Deshpande | A61M 25/007 604/523 |
| 2015/0273130 | A1 * | 10/2015 | McDermott | A61M 25/0108 604/526 |

FOREIGN PATENT DOCUMENTS

| | | | |
|---|---|---|---|
| JP | 2001-104486 | A | 4/2001 |
| JP | 2006-513803 | A | 4/2006 |
| JP | 2018198930 | A | * 12/2018 |

OTHER PUBLICATIONS

Partial European Search Report for related European Patent Application No. 20822003.8, dated May 18, 2022.

International Search Report for corresponding Application No. PCT/JP2020/021372, mailed Jul. 21, 2020.

Office Action dated Apr. 24, 2023 in corresponding European Patent Application No. 20822003.8.

* cited by examiner

DOUBLE-LUMEN CATHETER

TECHNICAL FIELD

The present disclosure relates to a double lumen catheter.

BACKGROUND ART

In the field of hemodialysis, blood is extracted from a blood vessel of a subject, treated outside the body, and then returned to the blood vessel. If urgent dialysis is performed or shunting is difficult, the blood is removed and returned using a catheter inserted into the blood vessel.

In such a case, a double lumen catheter is used which includes a blood removal passage and a blood return passage. The double lumen catheter is required to achieve high insertability, a decrease in poor blood removal and return, a decrease in recirculation, and other purposes.

In order to meet these requirements, displacing the positions of the end holes of the blood removal passage and the blood return passage to each other or providing side holes in the side wall of a catheter are considered (see, e.g., Patent Document 1).

CITATION LIST

Patent Document

PATENT DOCUMENT 1: Japanese Unexamined Patent Publication No. 2001-104486

SUMMARY OF THE DISCLOSURE

Technical Problems

In double lumen catheters, the blood removal and return passages are generally determined in advance. However, if a double lumen catheter is left in a blood vessel for a long time period, reverse connection of temporarily switching the blood removal and return passages may be performed to deal with occlusion or stenosis. An end hole displaced to reduce recirculation in forward connection may cause more recirculation in reverse connection.

Sticking of a catheter to a blood vessel wall causes blood removal failure. In addition, a thrombus may occur due to stagnation of blood. A catheter free from not only recirculation but also from these problems is required.

It is an objective of the present disclosure to achieve a double lumen catheter that hardly sticks to a blood vessel wall and causes less recirculation.

Solutions to the Problems

A double lumen catheter according to a first aspect of the present disclosure includes: a circumferential wall forming a lumen extending from a proximal end to a distal end; and a partition dividing the lumen into a first passage and a second passage extending in a longitudinal direction. Distal ends of the first passage and the second passage of the circumferential wall are aligned with each other. The partition includes a projection projecting beyond the distal end of the circumferential wall. The first passage has, at the distal end, a first passage slit formed by cutting out a part of the circumferential wall around a circumferential center of the circumferential wall.

The double lumen catheter according to the first aspect includes the projection, which reduces recirculation. The double lumen catheter further includes the first passage slit formed by cutting out a part of the circumferential wall, and thus hardly sticks to a blood vessel wall.

In the double lumen catheter according the first aspect, the second passage may have, at the distal end, a second passage slit formed by cutting out a part of the circumferential wall around the circumferential center of the circumferential wall. With this configuration, the double lumen catheter more hardly sticks to a blood vessel wall.

In this case, lengths of the first passage slit and the second passage slit are different from each other. In this configuration, the proximal ends of the slits are not aligned in the longitudinal direction, which causes less recirculation at the time of forward or reverse connection. This further reduces the recirculation.

In the double lumen catheter according the first aspect, the first passage may have the first passage through-hole being closer to the proximal end than the first passage slit is and penetrating the circumferential wall, and with this configuration, the double lumen catheter more hardly sticks to a blood vessel wall at the first passage slit.

In this case, the first passage through-hole may include a plurality of first passage through-holes in a zigzag pattern. With this configuration, the double lumen catheter more hardly sticks to a blood vessel wall at the first passage through-holes. Adjacent two of the first passage through-holes may be arranged on opposite sides of the first passage slit.

In the double lumen catheter according the first aspect, the second passage may have, at the distal end, a plurality of second passage through-holes penetrating the circumferential wall and arranged in a zigzag pattern. With this configuration, the double lumen catheter more hardly sticks to a blood vessel wall. Adjacent two of the second passage through-holes may be arranged on opposite sides of the first passage slit. This configuration further reduces the sticking at the time of reverse connection.

In this case, one of the second passage through-holes closest to the proximal end may be closer to the proximal end than the first passage slit is. This configuration further reduces the recirculation at the time of reverse connection.

In this case, the first passage may have the first passage through-hole being closer to the proximal end than the first passage slit is and penetrating the circumferential wall. One of the first passage through-holes closest to the distal end and one of the second passage through-holes closest to the proximal end may be arranged on opposite sides of the first passage slit. This configuration further reduces the recirculation.

A double lumen catheter according to a third aspect of the present disclosure may include: a circumferential wall forming a lumen extending from a proximal end to a distal end; and a partition dividing the lumen into a first passage and a second passage extending in a longitudinal direction. Distal ends of the first passage and the second passage of the circumferential wall may be aligned with each other. The first passage and the second passage may have, at the distal ends, a first passage slit and a second passage slit, respectively, each formed by cutting out a part of the circumferential wall from an end closer to the partition. Distal end surfaces of the circumferential wall and the partition may form a substantially S-shape as viewed from the distal end. This configuration reduces recirculation.

In the double lumen catheter according the third aspect, the first passage slit and the second passage slit may be arranged on opposite sides in a circumferential direction. This configuration further reduces the recirculation.

In the double lumen catheter according the third aspect, each of the first passage slit and the second passage slit may have a smaller slit width at the distal end than at the proximal end. With this configuration, the double lumen catheter reduces the removal blood pressure around the proximal end of each slit and more hardly sticks to a blood vessel wall.

A tunneler according to an aspect of the present disclosure includes: a shaft; and a connector at a proximal end of the shaft, the connector being connected to a double lumen catheter, the double lumen catheter including a partition dividing a lumen surrounded by a circumferential wall into two passages and having a projection projecting toward a distal end of the circumferential wall, the connector including: an insertion portion to be inserted and fitted into one of the two passages; and a non-insertion portion between the insertion portion and the shaft, and the non-insertion portion having an outer diameter smaller than an outer diameter of the proximal end of the shaft and larger than an outer diameter of the distal end of the insertion portion, and a length greater than or equal to a length of the projection.

With this configuration, the tunneler is easily connectable to a double lumen catheter having a projection.

In the tunneler according to an aspect, a difference between radii of the non-insertion portion and the insertion portion is smaller than or equal to a thickness of the partition of the double lumen catheter. This configuration reduces bending of the projection.

A tunneler according to another aspect of the present disclosure includes: a shaft; an insertion portion at a proximal end of the shaft so as to be inserted into one of passages of a double lumen catheter; and a curved portion connecting the shaft and the insertion portion, center axes of the shaft and the double lumen catheter coinciding with each other, when the insertion portion is inserted into the one of the passages of the double lumen catheter. This configuration facilitates the covering of the connector with the sheath.

A catheter complex according to an aspect of the present disclosure includes the double lumen catheter and tunneler according to the present disclosure.

The catheter complex according to the aspect may further include: a sheath covering the connector between the double lumen catheter and the tunneler.

Advantages of the Invention

The double lumen catheter according to the present disclosure hardly sticks and causes less recirculation.

DESCRIPTION OF EMBODIMENTS

Figure 1:
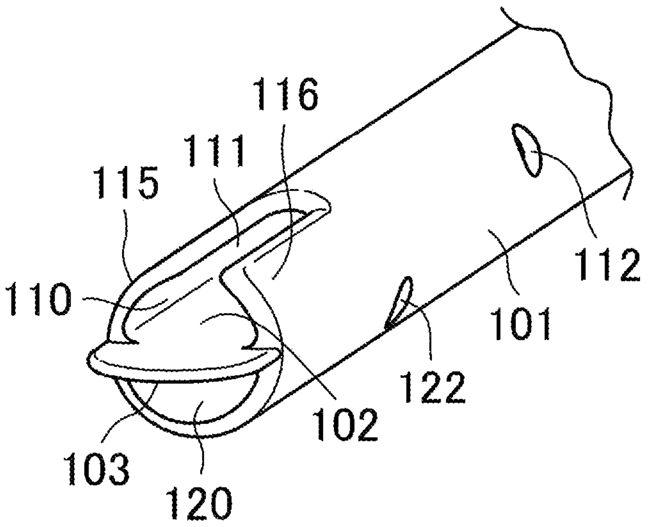
FIG. 1 is a perspective view of a double lumen catheter according to a first embodiment.
Figure 2:
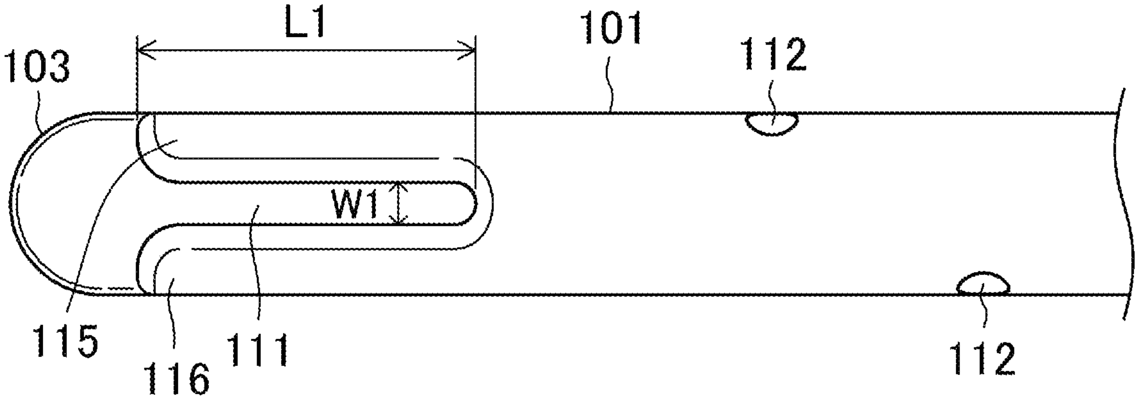
FIG. 2 is a top view of the double lumen catheter according to the first embodiment.
Figure 3:
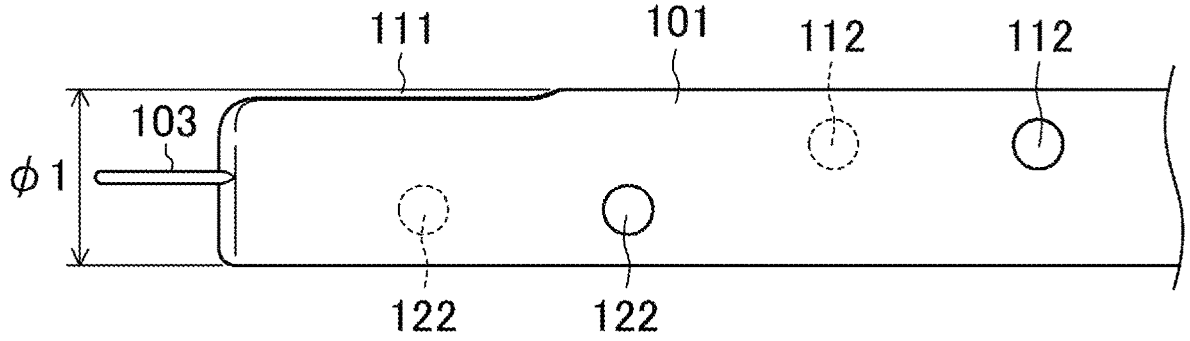
FIG. 3 is a side view of the double lumen catheter according to the first embodiment.
Figure 4:
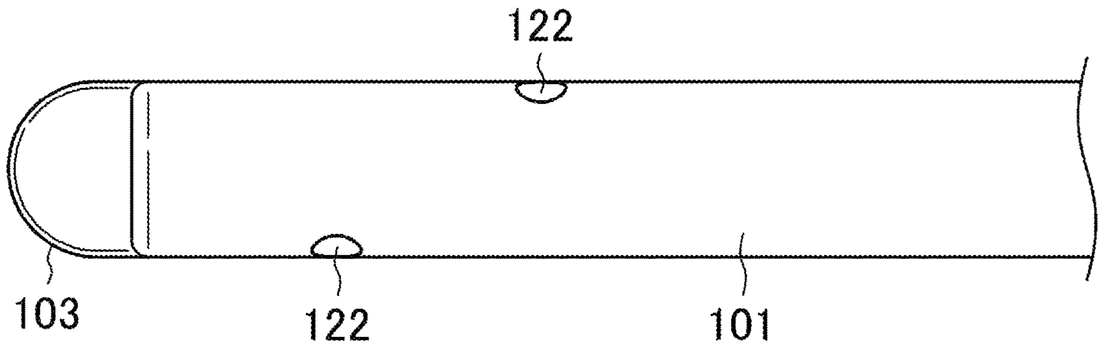
FIG. 4 is a bottom view of the double lumen catheter according to the first embodiment.

As shown in FIGS. 1 to 5, a double lumen catheter according to a first embodiment is a tube made of resin or other materials, and includes a circumferential wall 101 and a partition 102. The circumferential wall 101 forms a lumen extending from a proximal end to a distal end. The partition 102 divides the lumen into a first passage 110 and a second passage 120. The distal ends of the first passage 110 and the second passage 120 of the circumferential wall 101 are aligned with each other. The positions of end holes in the first passage 110 and the second passage 120 are thus aligned with each other. The partition 102 has a projection 103 projecting beyond the distal end of the circumferential wall 101 and having a U-shaped plane.

In the double lumen catheter according to this embodiment, the distal ends of the first passage 110 and the second passage 120 of the circumferential wall 101 are aligned with each other, which reduces recirculation at the time of reverse connection. The projection 103 provides the advantage of further reducing the recirculation.

The double lumen catheter according to this embodiment includes a first passage slit 111 and a plurality of first passage through-holes 112 at the distal end of the first passage 110, and a plurality of second passage through-holes 122 at the distal end of the second passage 120. The distal end of the circumferential wall 101 has a first distal end circumferential wall 115 and a second distal end circumferential wall 116 with the first passage slit 111 interposed therebetween. The second passage through-holes 122 are interposed between the distal end of the first passage slit 111 and the first passage through-holes 112. More specifically, the one of the second passage through-holes 122 closest to the proximal end is interposed between the proximal end of the first passage slit 111 and the one of the first passage through-holes closest to the distal end.

The double lumen catheter according to this embodiment has the first passage slit 111. When the first passage 110 serves as a blood removal lumen, the flow of blood sucked into the first passage 110 is dispersed not to be concentrated in the end hole at the distal end. This configuration reduces the recirculation of the blood flowing out of the distal end of the second passage 120 to be directly sucked into the first passage 110. In addition, the dispersed blood flow hardly causes the sticking of the catheter to a blood vessel wall. With an increase in the number of openings, less occlusion is caused by thrombus.

The double lumen catheter according to this embodiment includes the first and second distal end circumferential walls 115 and 116 with the first passage slit 111 interposed therebetween which is located around the circumferential center of the circumferential wall 101. This configuration reduces a decrease in the rigidity of the first passage slit 111 and the occlusion or stenosis of the distal end of the circumferential wall 101 caused by the pressure from the blood vessel wall or other portions in the use of the catheter.

The first passage 110 has the first passage through-holes 112. This configuration further disperses the flow of the blood sucked into the first passage 110, which hardly causes the sticking of the catheter to a blood vessel wall. In view of reducing the sticking to a blood vessel wall, the first passage through-holes 112 are displaced from the first passage slit 111 as much as possible in one preferred embodiment. The sticking to a blood vessel wall is further reduced by arranging the first passage through-holes 112 in a zigzag pattern. If the first passage through-holes 112 are arranged in a zigzag pattern, adjacent two of the first passage through-holes 112 are displaced from each other as much as possible in one preferred embodiment. For example, the angle formed by the straight lines connecting the adjacent two of the first passage through-holes 112 and the center of the circle formed by the circumferential wall 101 ranges from 120° to 180° in one preferred embodiment. However, the first passage through-holes 112 may be arranged in series in the longitudinal direction.

When the first passage 110 serves as the blood return lumen, the first passage slit 111 disperses the outflowing blood. This configuration hardly causes the recirculation of the blood flowing out of the first passage 110 to be directly sucked into the end hole of the second passage 120. The one of the second passage through-holes 122 at the distal end of the second passage 120 disperses the flow of blood sucked into the second passage 120 as well. This configuration further reduces the rate of recirculation at the time of reverse connection. In view of this, the one of the second passage through-holes closest to the proximal end is located closer to the proximal end than the first passage slit 111 is in one preferred embodiment. The second passage through-holes 122 reduce the sticking to a blood vessel wall at the time of reverse connection. In view of reducing the sticking to a blood vessel wall, the second passage through-holes 122 are also arranged in a zigzag pattern in one preferred embodiment. In this case, adjacent two of the second passage through-holes 122 are displaced from each other as much as possible in one preferred embodiment. For example, the angle formed by the straight lines connecting adjacent two of the second passage through-holes 122 and the center of the circle formed by the circumferential wall 101 ranges from 120° to 180° in one preferred embodiment.

Even if the distal end of the second passage 120 is closed by a thrombosis or other causes, the second passage through-holes 122 keep the second passage 120 open.

In view of reducing recirculation, the one of the second passage through-holes 122 closest to the proximal end is closer to the distal end than the one of the first passage through-holes 112 closest to the distal end is, and closer to the proximal end than the proximal end of the first passage slit 111 is in one preferred embodiment. Assume that both of the first and second passage through-holes 112 and 122 are arranged in a zigzag manner. In this case, in view of further reducing the recirculation, the one of the second passage through-holes 122 closest to the proximal end and the one of the first passage through-holes 112 closest to the distal end are arranged on opposite sides of the first passage slit 111 in one preferred embodiment.

The double lumen catheter according to this embodiment includes the first passage slit 111 around the circumferential center of the first passage 110 of the circumferential wall 101. With this configuration, the first and second distal end circumferential walls 115 and 116 are formed on respective sides of the first passage slit 111. The first passage slit 111 around the circumferential center reduces the rigidity of at least one of the first or second distal end circumferential wall 115 or 116, which reduces the occlusion of the end hole of the first passage 110 when the catheter is left in a blood vessel. The width W1 of the first passage slit 111 is not particularly limited, but may be about 15% to about 35% of the outer diameter ϕ1 of the catheter in one preferred embodiment. The length L1 of the first passage slit 111 is not particularly limited, but may be about 1.5 times to about 2.5 times the outer diameter ϕ1 of the catheter in one preferred embodiment. In this embodiment, the outer diameter ϕ1 of the catheter is 4.3 mm. The width W1 and the length L1 of the first passage slit 111 are 1 mm and 8 mm, respectively. In one preferred embodiment, the first passage slit 111 has a wall surface with rounded corners.

The first passage through-holes 112 are side holes penetrating the circumferential wall 101 and connecting the first passage 110 to the outside, and are arranged at intervals in the longitudinal direction. While an example will be described in this embodiment where two first passage through-holes 112 are provided, three or more first passage through-holes 112 may be provided. In this embodiment, adjacent two of the first passage through-holes 112 are arranged to be displaced from each other in the longitudinal and transverse directions of the first passage 110, that is, arranged in a zigzag pattern, and further alternately arranged on opposite sides of the first passage slit 111. The first passage through-holes 112 may be arranged at equal or unequal intervals in the longitudinal direction.

The second passage through-holes 122 are side holes penetrating the circumferential wall 101 and connecting the second passage 120 to the outside, and are arranged at intervals in the longitudinal direction. While an example will be described in this embodiment where two second passage through-holes 122 are provided, three or more second passage through-holes 122 may be provided. The second passage through-holes 122 are also arranged in a zigzag pattern. The one of the second passage through-holes 122 closest to the proximal end is located on the opposite side of the first passage slit 111 to the one of the first passage through-holes 112 closest to the distal end in one preferred embodiment. The first and second passage through-holes 112 and 122 are, as a whole, arranged in a zigzag pattern in one more preferred embodiment.

The one of the second passage through-holes 122 closest to the distal end is spaced apart from the distal end of the circumferential wall 101 to some extent in one preferred embodiment. Specifically, the distance from the distal end of the circumferential wall to the center of the one of the second passage through-holes 122 closest to the distal end may be about 0.8 times to about 1.5 times the outer diameter ϕ1 of the catheter in one preferred embodiment. All the first and second passage through-holes 112 and 122 may be arranged at equal intervals in the longitudinal direction in one preferred embodiment. In this case, the distance between the centers of the adjacent through-holes may be about 3.5 times to about 5.5 times the diameter of the through-holes in one preferred embodiment. For example, if the outer diameter ϕ1 of the catheter is 4.3 mm, the through-holes may be arranged at the intervals of 5 mm. Note that the intervals of the first and second passage through-holes 112 and 122 in the longitudinal direction may be different. All the first and second passage through-holes 112 and 122 may be arranged at unequal intervals. The diameter(s) of the first and second passage through-holes 112 and 122 is not particularly limited but may be about 15% to about 35% of the outer diameter ϕ1 of the catheter in one preferred embodiment.

The diameters of the first and second passage through-holes 112 and 122 may be the same or different. Some of the diameters of the first and second passage through-holes 112 and 122 may be different.

Figure 6:
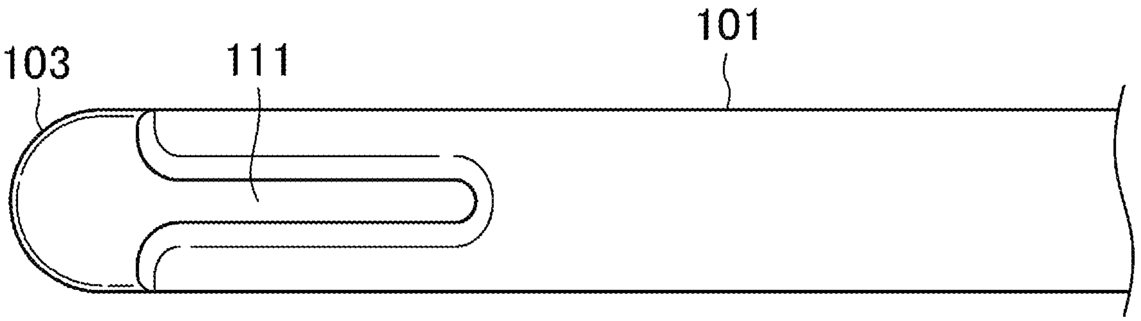
FIG. 6 is a top view of a double lumen catheter according to a first variation of the first embodiment.
Figure 7:
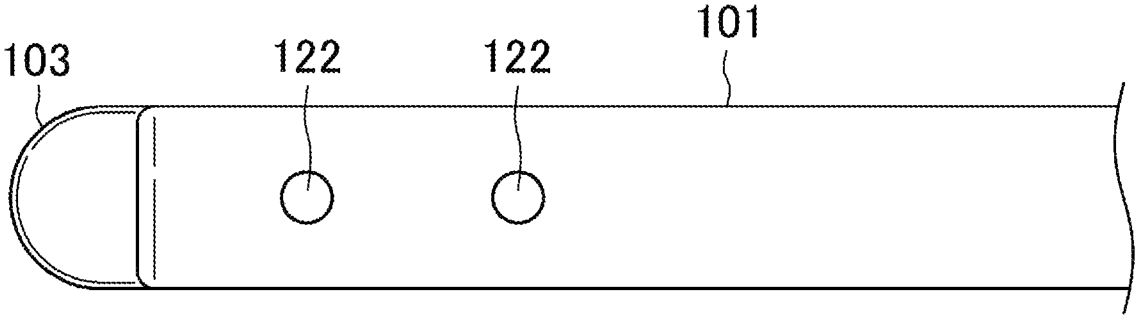
FIG. 7 is a bottom view of the double lumen catheter according to the first variation of the first embodiment.

There may be variations of the double lumen catheter according to this embodiment. For example, as in a first variation shown in FIGS. 6 and 7, no first passage through-holes 112 may be provided. In the first variation, the second passage through-holes 122 are arranged in series but may be arranged in a zigzag pattern.

Figure 8:
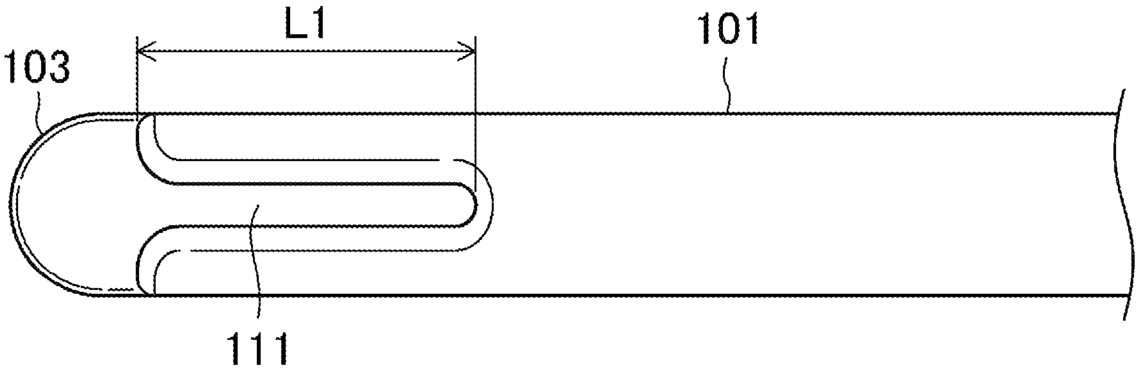
FIG. 8 is a top view of a double lumen catheter according to a second variation of the first embodiment.
Figure 9:
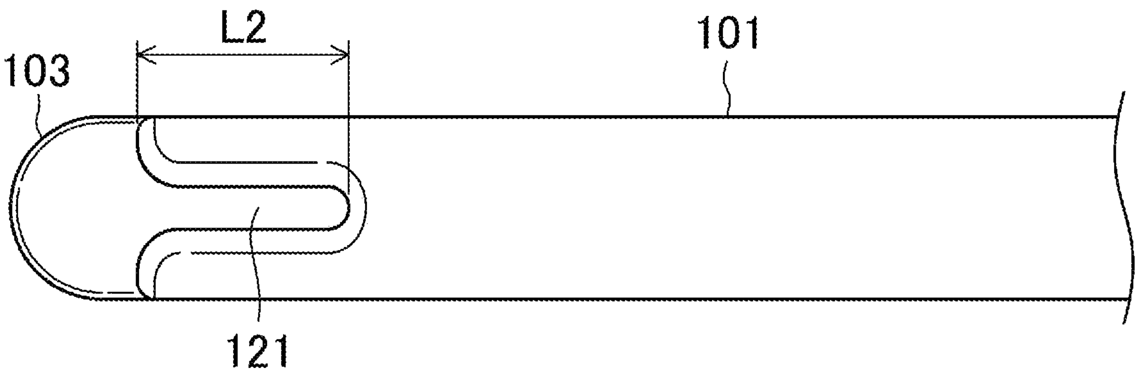
FIG. 9 is a bottom view of the double lumen catheter according to the second variation of the first embodiment.

As in a second variation shown in FIGS. 8 and 9, the second passage through-holes 122 may be replaced with a second passage slit 121. When serving as a blood removal lumen, the second passage 120 with the slit less sticks to a blood vessel wall. The second passage slit 121 may have, in the longitudinal direction, a length L2 that is shorter than the length L1 of the first passage slit 111. Specifically, L2 may be about 80% to about 45% of L1 in one preferred embodiment. Note that L2 may be the same as L1. One of the first passage through-holes 112 or the second passage through-holes 122 may be provided.

Figure 10:
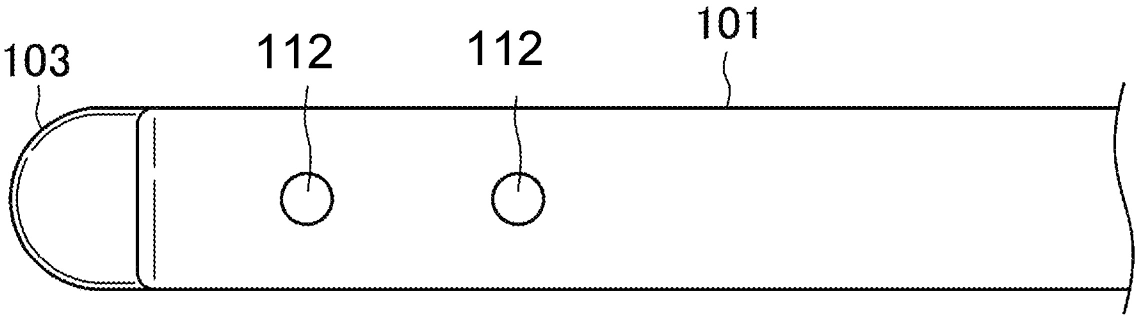
FIG. 10 is a top view of a double lumen catheter according to a third variation of the first embodiment.
Figure 11:
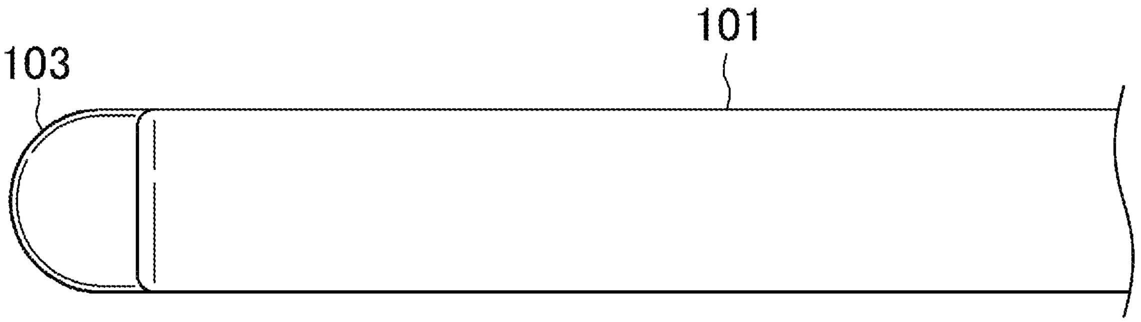
FIG. 11 is a bottom view of the double lumen catheter according to the third variation of the first embodiment.

The second passage may include neither the second passage through-holes nor the second passage slit. As in a third variation shown in FIGS. 10 and 11, the first passage slit 111 may be replaced with the first passage through-holes 112. In this case as well, the second passage 120 may have at least one of the second passage through-holes 122 or the second passage slit 121.

An example has been described in this embodiment and variations where the projection 103 has the U-shaped plane without any corner. The projection 103 is not necessarily in such the shape but may have a rectangular or trapezoidal plane with corners.

Figure 12:
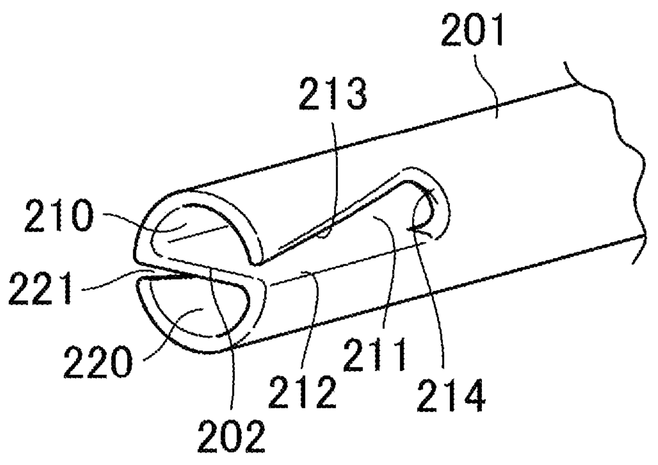
FIG. 12 is a perspective view of a double lumen catheter according to a second embodiment.
Figure 13:
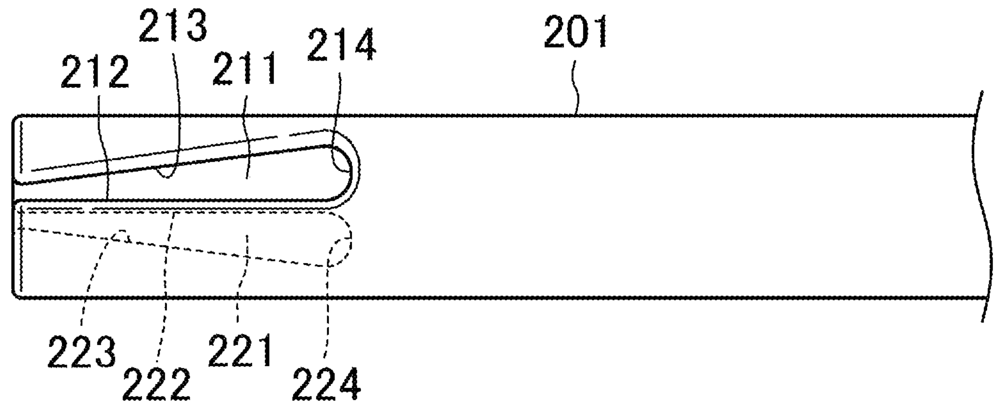
FIG. 13 is a side view of the double lumen catheter according to the second embodiment.

FIGS. 12 and 13 show a double lumen catheter according to a second embodiment. In the double lumen catheter according to the second embodiment, first and second passages 210 and 220 include first and second passage slits 211 and 221, respectively. Each of the first and second passage slits 211 and 221 is formed by cutting out a part of a circumferential wall 201 from an end closer to a partition 202. The first and second passage slits 211 and 221 are arranged on opposite sides in a circumferential direction. The distal end surfaces of the circumferential wall 201 and the partition 202 form a substantially S-shape when the lumen catheter according the second embodiment is viewed from the distal end of the double lumen catheter according to the second embodiment.

The first and second passage slits 211 and 221 include partition-side slit lines 212 and 222, opposed slit lines 213 and 223, and connecting slit lines 214 and 224, respectively. Each of the connecting slit lines 214 and 224 is in a substantially U-shape. In this embodiment, the partition-side slit lines 212 and 222 substantially coincide with the surfaces of the partition 202. The configuration is not limited to such the aspect. The circumferential wall may exist between each of the partition-side slit lines 212 and 222 and the associated one of the surfaces of the partition 202.

The first and second passage slits 211 and 221 are arranged on opposite sides in the circumferential direction. This configuration separates the blood flows for removal and return and hardly causes recirculation when the first passage 210 serves as a blood removal lumen or a blood return lumen.

In this embodiment, each of the first and second passage slits 211 and 221 has a smaller width (i.e., slit width) at the distal end than at the proximal end of the circumferential wall 201. Accordingly, the phenomenon hardly occurs that the distal end of the passages serving as the blood removal lumen is crushed largely and causes occlusion. Each slit with the greater slit width at the proximal end reduces the concentration of the removal blood pressure around the connecting slit line 214, 224. Note that each of the first and second passage slits 211 and 221 may have a constant slit width or a greater slit width at the distal end than at the proximal end.

The maximum slit width of the first and second passage slits 211 and 221 is not particularly limited but may be about 15% to about 35% of the outer diameter ϕ1 of the catheter in one preferred embodiment. The length of each slit is not particularly limited but may be about 1.5 times to about 2.5 times the outer diameter ϕ1 of the catheter in one preferred embodiment.

The double lumen catheter according to the second embodiment may also have one of the first or second passage through-holes. The first and second passage through-holes may be arranged as in the first embodiment and its variations. In the double lumen catheter according to the second embodiment as well, the partition 202 may have a projection.

The double lumen catheter according to the embodiments and variations is left within a blood vessel to be used for removing and returning blood, if dialysis is performed without shunting. A hub, connector, or other items may be connected to the proximal end of the catheter as necessary.

The double lumen catheter according to the embodiments and variations may serves as a catheter complex including a tunneler, connected at the distal end, for tunneling under a skin. The tunneler at the distal end forms a subcutaneous tunnel. After introducing the double lumen catheter into the subcutaneous tunnel, the tunneler is removed so that the double lumen catheter extends through the subcutaneous tunnel into the blood vessel. The tunneler to be connected is not particularly limited but may be the one shown in FIG. 14, for example.

Figure 14:
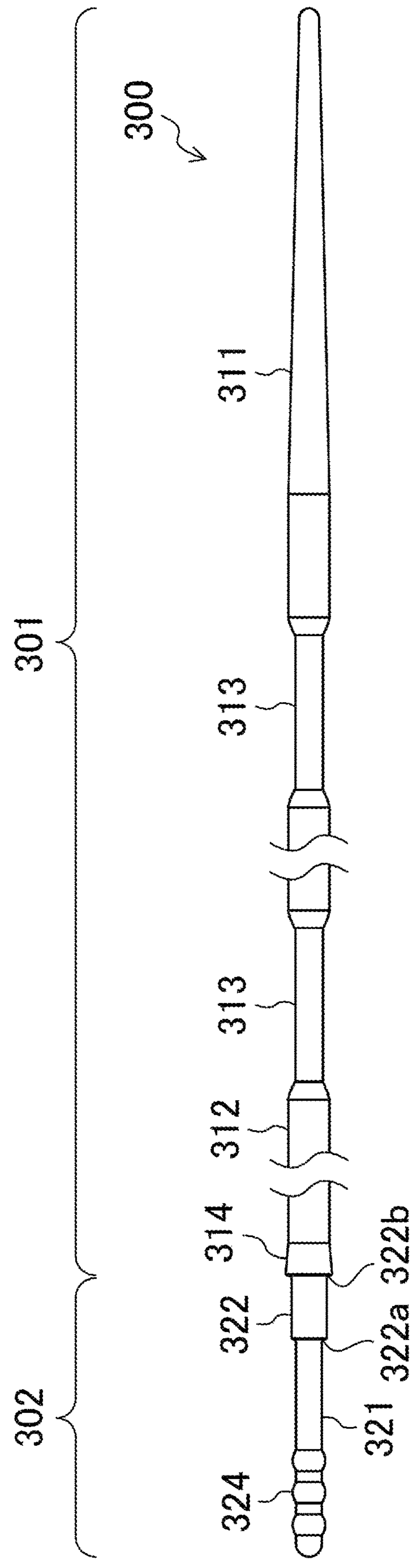
FIG. 14 is a side view of a tunneler according to an embodiment.

A tunneler 300 shown in FIG. 14 includes a shaft 301 and a connector 302 at the proximal end of the shaft 301. The shaft 301 includes a tapered distal end 311, a body 312 with a constant diameter, and thinner parts 313. The shaft 301 includes, at the proximal end, a tapered portion 314 as a stopper of a sheath.

The thinner parts 313 facilitate bending of the shaft 301. Although two thinner parts 313 are shown in FIG. 14, one, three or more thinner parts 313 may be provided. Alternatively, no thinner part may be provided.

The connector 302 includes an insertion portion 321 to be inserted into the double lumen catheter, and a non-insertion portion 322 between the insertion portion 321 and the shaft 301.

The insertion portion 321 has a smaller outer diameter than the non-insertion portion 322, and has a maximum outer diameter to be inserted and fitted into the first or second passage of the double lumen catheter. In FIG. 14, the insertion portion 321 has, at the proximal end, a thicker part 324 with a larger diameter than other parts not to allow the inserted catheter to easily come out of the insertion portion 321. As long as not coming out after being inserted into the double lumen catheter, the insertion portion 321 may be in the shape of a taper with the diameter gradually decreasing from the distal end toward the proximal end, in the shape of a bamboo shoot, or other shapes.

Figure 5:
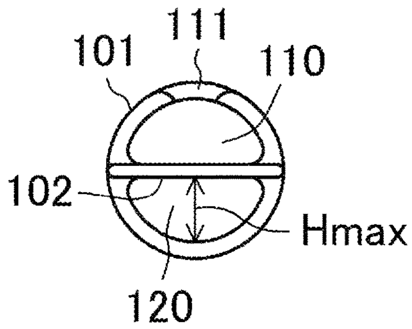
FIG. 5 is a front view of the double lumen catheter according to the first embodiment.

The insertion portion 321 has, at least at the proximal end, an outer diameter slightly smaller than the maximum heights of the first and second passages of the double lumen catheter in one preferred embodiment for the ease of inserting the insertion portion 321. The insertion portion 321 (the thicker part 324) has the maximum outer diameter slightly larger than the maximum heights of the first and second passages of the double lumen catheter in one preferred embodiment not to allow the insertion portion 321 to come out of the catheter. The length of the insertion portion 321 is not particularly limited but may be preferably 5 mm or more not to allow the insertion portion 321 to come out, and preferably 25 mm or less for the ease of handling. The maximum height $H_{max}$ of each passage is the maximum vertical distance from the surface of the partition to the inner surface of the circumferential wall as shown in FIG. 5.

The non-insertion portion 322 has a larger outer diameter than the end of the insertion portion 321 closer to the non-insertion portion 322. There is a first step 322*a* between the insertion portion 321 and the non-insertion portion 322. On the other hand, the non-insertion portion 322 has a smaller outer diameter than the proximal end of the tapered portion 314 located at the proximal end of the shaft 301. There is a second step 322*b* between the non-insertion portion 322 and the shaft 301.

When a catheter complex with a tunneler connected is used for forming a subcutaneous tunnel, the tunneler is generally used after being inserted into a sheath to cover the connector connecting the tunneler to the distal end of the catheter. It is thus important to connect the catheter and the tunneler as flat as possible (without any unevenness) to be inserted into the sheath.

A typical tunneler without any non-insertion portion 322 has a larger step between the connector and the shaft. If the typical tunneler is inserted into a double lumen catheter having a projection, the larger step between the connector and the shaft largely bends the projection largely outward. The projection thus comes out of the sheath and fails to cover the connector.

The tunneler 300 according to this embodiment has the smaller first step 322*a*. Even if the tunneler 300 is, until the root of the insertion portion 321, inserted into the double lumen catheter, the projection neither is largely bent nor comes out of the sheath. The non-insertion portion 322 secures the space for the projection, and the distance from the distal end of the double lumen catheter to the shaft 301, which facilitates radial movement at the time of covering with the sheath. The step 322*b* between the non-insertion portion 322 and the tapered portion 314 does not allow the projection and the sheath arranged along the non-insertion portion 322 to abut on each other along the end surface. Accordingly, the connector is smoothly inserted into the sheath.

The non-insertion portion 322 has an outer diameter larger than the maximum height or width of the first or second passage in one preferred embodiment not to allow the non-insertion portion 322 to enter the inside of the first or second passage of the double lumen catheter. On the other hand, in view of smooth insertion into the sheath, the distal end of the projection of the catheter bent by the first step 322*a* does not exceed the circumferential wall of the passage that is not connected to the tunneler in one preferred embodiment. The non-insertion portion 322 has a length equal to or longer than the length of the projection of the double lumen catheter in one preferred embodiment. The second step 322*b* has a size equal to or greater than the thickness of the projection in one preferred embodiment.

The maximum outer diameter of the insertion portion 321 and the outer diameter of the non-insertion portion are not particularly limited. In view of providing the advantages described above, the maximum outer diameter of the insertion portion 321 may be about 1.1 times to about 1.4 times the maximum height $H_{max}$ of each passage, and the outer diameter of the non-insertion portion may be about 1.5 times to about 1.9 times the maximum height $H_{max}$ of each passage in one preferred embodiment.

In a double lumen catheter where the first and second passages have the same maximum height and the distal ends of the first and second passages are aligned with each other, the insertion portion 321 may be inserted into any of the first and second passages. If one of the passages has a slit, the insertion portion may be inserted into the other passage without any slit in one preferred embodiment, because the insertion portion 321 hardly comes out.

Even when used in combination with a double lumen catheter with a projection, the tunneler 300 according to this embodiment is inserted into the sheath smoothly, which facilitates the placement of the catheter. The tunneler 300 according to this embodiment may be used in combination with a double lumen catheter without any projection.

Figure 15:
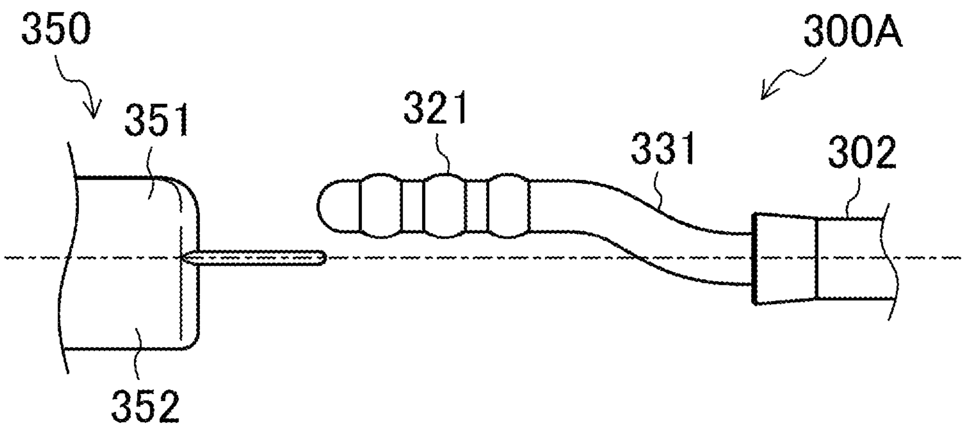
FIG. 15 is a side view of a tunneler according to a variation.

The double lumen catheters according to the embodiments may be used in combination with a tunneler 300A shown in FIG. 15. The tunneler 300A includes: a shaft 301; an insertion portion 321 to be inserted into one of first and second passages 351 and 352 of a double lumen catheter 350; and a curved portion 331 curved in a substantially S-shape between the shaft 301 and the insertion portion 321. The curved portion 331 is configured so that the center axes of the shaft 301 and the double lumen catheter 350 coincide with each other, when the insertion portion 321 is inserted into the one of the passages of the double lumen catheter 350. This configuration causes no significant unevenness between the tunneler and the double lumen catheter, and easily covers the connector between the double lumen catheter and the tunneler using the sheath. The phase “the center axes . . . coincide with each other” here not only means that the center axes completely overlap each other but also includes the case where the center axes are displaced from each other by about several millimeters in any direction without hindering the insertion into the sheath.

INDUSTRIAL APPLICABILITY

The double lumen catheter according to the present disclosure hardly sticks to a blood vessel wall and causes less recirculation, and is thus useful as a hemodialysis catheter, for example.

DESCRIPTION OF REFERENCE CHARACTERS

- 101 Circumferential Wall
- 102 Partition
- 103 Projection
- 110 First Passage
- 111 First Passage Slit
- 112 First Passage Through-Hole
- 115 First Distal End Circumferential Wall
- 116 Second Distal End Circumferential Wall
- 120 Second Passage
- 121 Second Passage Slit
- 122 Second Passage Through-Hole
- 201 Circumferential Wall
- 202 Partition
- 210 First Passage

211 First Passage Slit
212 Partition-Side Slit Line
213 Opposed Slit Line
214 Connecting Slit Line
220 Second Passage
221 Second Passage Slit
222 Partition-Side Slit Line
223 Opposed Slit Line
224 Connecting Slit Line
300 Tunneler
301 Shaft
302 Connector
311 Distal End
312 Body
313 Thinner Part
314 Tapered Portion
321 Insertion Portion
322 Non-Insertion Portion
**322*a*** First Step
**322*b*** Second Step
324 Thicker Part
331 Curved Portion

The invention claimed is:

1. A double lumen catheter comprising:

a circumferential wall forming a lumen extending from a proximal end to a distal end; and a partition dividing the lumen into a first passage and a second passage extending in a longitudinal direction, distal ends of the first passage and the second passage of the circumferential wall being aligned with each other, the partition including a projection projecting beyond the distal end of the circumferential wall, the first passage having, at a distal tip of the distal end, a first passage slit provided on a center portion of the circumferential wall between two connections of the circumferential wall and the partition, and the second passage having no slit, wherein the first passage has a first passage through-hole being closer to the proximal end than the first passage slit is and penetrating the circumferential wall, and wherein the first passage through-hole includes a plurality of first passage through-holes in a zigzag pattern.

2. The double lumen catheter of claim 1, wherein adjacent two of the first passage through-holes are arranged on opposite sides of the first passage slit.

3. A catheter complex comprising:

the double lumen catheter of claim 1; and a tunneler has a shaft; and a connector at a proximal end of the shaft, the connector being connected to the double lumen catheter, wherein the connector includes an insertion portion to be inserted and fitted into one of the two passages; and a non-insertion portion between the insertion portion and the shaft, and the non-insertion portion has an outer diameter smaller than an outer diameter of the proximal end of the shaft and larger than an outer diameter of a distal end of the insertion portion, and a length greater than or equal to a length of the projection.

4. The catheter complex of claim 3, further comprising:

a sheath covering the connector between the double lumen catheter and the tunneler.

5. A double lumen catheter comprising: The double lumen-catheter of claim 1, wherein a circumferential wall forming a lumen extending from a proximal end to a distal end; and a partition dividing the lumen into a first passage and a second passage extending in a longitudinal direction, distal ends of the first passage and the second passage of the circumferential wall being aligned with each other, the partition including a projection projecting beyond the distal end of the circumferential wall, the first passage having, at a distal tip of the distal end, a first passage slit provided on a center portion of the circumferential wall between two connections of the circumferential wall and the partition, and the second passage having no slit, wherein the second passage has, at the distal end, a plurality of second passage through-holes penetrating the circumferential wall and arranged in a zigzag pattern.

6. The double lumen catheter of claim 5, wherein adjacent two of the second passage through-holes are arranged on opposite sides of the first passage slit.

7. The double lumen catheter of claim 5, wherein one of the second passage through-holes closest to the proximal end is closer to the proximal end than the first passage slit is.

8. The double lumen catheter of claim 5, wherein the first passage has a plurality of first passage through-holes being closer to the proximal end than the first passage slit is and penetrating the circumferential wall, and one of the plurality of first passage through-holes closest to the distal end and one of the plurality of second passage through-holes closest to the proximal end are arranged on opposite sides of the first passage slit.

* * * * *